(12) United States Patent
Kerwin

(10) Patent No.: US 10,996,167 B2
(45) Date of Patent: May 4, 2021

(54) CONTAINER WITH LUMINESCENT SUNSCREEN AND CLOSURE WITH ILLUMINATOR

(71) Applicant: Michael Kerwin, Hinesville, GA (US)

(72) Inventor: Michael Kerwin, Hinesville, GA (US)

( * ) Notice: Subject to any disclaimer, the term of this patent is extended or adjusted under 35 U.S.C. 154(b) by 0 days.

(21) Appl. No.: 15/867,338

(22) Filed: Jan. 10, 2018

(65) Prior Publication Data
US 2019/0212270 A1 Jul. 11, 2019

(51) Int. Cl.
| | |
|---|---|
| *G01N 21/64* | (2006.01) |
| *B65D 41/04* | (2006.01) |
| *B65D 85/00* | (2006.01) |
| *B65D 55/00* | (2006.01) |
| *A61K 8/49* | (2006.01) |
| *A61K 8/27* | (2006.01) |
| *F21V 23/04* | (2006.01) |
| *F21L 4/00* | (2006.01) |

(Continued)

(52) U.S. Cl.
CPC .......... *G01N 21/6447* (2013.01); *A61C 17/04* (2013.01); *A61K 8/27* (2013.01); *A61K 8/498* (2013.01); *B65D 41/04* (2013.01); *B65D 55/00* (2013.01); *B65D 85/70* (2013.01); *F21L 4/00* (2013.01); *F21V 23/0414* (2013.01); *A61K 2800/81* (2013.01); *A61K 2800/87* (2013.01); *F21Y 2115/10* (2016.08); *G01N 2201/062* (2013.01)

(58) Field of Classification Search
CPC .......... G01N 21/6447; G01N 2201/062; G01T 1/02; G01J 1/429; G01J 1/50
See application file for complete search history.

(56) References Cited

U.S. PATENT DOCUMENTS

| | | | | |
|---|---|---|---|---|
| 3,899,677 A | * | 8/1975 | Hori | C08K 5/0016 250/474.1 |
| 3,903,423 A | * | 9/1975 | Zweig | A61B 5/0059 250/474.1 |

(Continued)

FOREIGN PATENT DOCUMENTS

| | | |
|---|---|---|
| CN | 102502064 A | 6/2012 |
| CN | 203461291 U | 3/2014 |

(Continued)

*Primary Examiner* — David P Porta
*Assistant Examiner* — Djura Malevic
(74) *Attorney, Agent, or Firm* — Law Offices of John G. Posa

(57) ABSTRACT

Apparatus for ensuring adequate sunscreen protection includes a light-activated sunscreen product, and an illuminator including a battery, a switch and a light source that causes the light-activated sunscreen product to glow when illuminated with the light source. The light-activated sunscreen product may include a zinc-oxide-based lotion and a fluorescent substance such as fluorescein dye causing the lotion to glow in any available color when applied to the skin and illuminated by the light source. The closure may be a cap with a threaded attachment to the container, and the light source may comprise one or more ultraviolet light-emitting diodes. The illuminator may be disposed in a cap with top and side surfaces, and the switch may be positioned on the side of the cap, and the light source on the top of the cap, or vice versa. The switch is preferably a momentary contact switch.

19 Claims, 4 Drawing Sheets

(51) Int. Cl.
*A61C 17/06* (2006.01)
*F21Y 115/10* (2016.01)

(56) References Cited

U.S. PATENT DOCUMENTS

| | | | | |
|---|---|---|---|---|
| 3,988,437 A * | 10/1976 | Bradner | | A61K 8/31 |
| | | | | 252/301.16 |
| 4,280,050 A | 7/1981 | Callender | | |
| 4,818,491 A * | 4/1989 | Fariss | | G01J 1/58 |
| | | | | 116/207 |
| 4,863,282 A * | 9/1989 | Rickson | | G01J 1/50 |
| | | | | 374/162 |
| 4,919,983 A * | 4/1990 | Fremin | | A61J 9/02 |
| | | | | 215/11.2 |
| 5,028,792 A * | 7/1991 | Mullis | | G01J 1/50 |
| | | | | 250/474.1 |
| 5,036,311 A * | 7/1991 | Moran | | G01J 1/429 |
| | | | | 250/372 |
| 5,117,116 A * | 5/1992 | Bannard | | G01J 1/50 |
| | | | | 250/472.1 |
| 5,365,068 A * | 11/1994 | Dickerson | | A61N 5/06 |
| | | | | 250/372 |
| 5,387,798 A * | 2/1995 | Funakoshi | | C09K 9/02 |
| | | | | 250/474.1 |
| 5,391,883 A * | 2/1995 | Kinsey | | G01J 1/04 |
| | | | | 250/372 |
| 5,435,307 A * | 7/1995 | Friauf | | A61B 5/0059 |
| | | | | 600/317 |
| 5,523,075 A * | 6/1996 | Fuerst | | A61K 8/046 |
| | | | | 424/59 |
| 5,543,137 A * | 8/1996 | Repper | | A61K 8/02 |
| | | | | 424/59 |
| 5,562,896 A * | 10/1996 | Repper | | A61K 8/02 |
| | | | | 424/59 |
| 5,567,420 A * | 10/1996 | McEleney | | A61K 8/4973 |
| | | | | 424/401 |
| D376,105 S * | 12/1996 | Thompson | | D9/529 |
| D376,547 S * | 12/1996 | McRae | | D10/78 |
| 5,581,090 A * | 12/1996 | Goudjil | | G01J 1/50 |
| | | | | 250/372 |
| 5,589,398 A * | 12/1996 | Krause | | G01J 1/50 |
| | | | | 422/423 |
| 5,609,852 A * | 3/1997 | Galley | | A61K 8/11 |
| | | | | 106/425 |
| 5,612,542 A * | 3/1997 | Brown | | G01J 1/50 |
| | | | | 250/474.1 |
| 5,626,839 A * | 5/1997 | Scales-Medeiros | | A61K 8/33 |
| | | | | 424/401 |
| 5,686,727 A * | 11/1997 | Reenstra | | A61F 5/028 |
| | | | | 250/227.11 |
| 5,720,555 A * | 2/1998 | Elele | | G01K 11/16 |
| | | | | 116/216 |
| 5,747,011 A * | 5/1998 | Ross | | A61K 8/06 |
| | | | | 424/400 |
| 5,802,015 A * | 9/1998 | Rothschild | | G04F 1/005 |
| | | | | 116/202 |
| 5,849,218 A * | 12/1998 | Johansen, Jr. | | C04B 41/5079 |
| | | | | 252/301.4 R |
| 5,986,273 A * | 11/1999 | Tripp | | G01J 1/50 |
| | | | | 250/474.1 |
| 5,997,891 A * | 12/1999 | Fuerst | | A61K 8/046 |
| | | | | 424/400 |
| 6,007,797 A * | 12/1999 | Bell | | A61K 8/06 |
| | | | | 424/400 |
| 6,046,455 A * | 4/2000 | Ribi | | G01J 1/50 |
| | | | | 250/336.1 |
| 6,086,858 A * | 7/2000 | McEleney | | A61K 8/4973 |
| | | | | 424/401 |
| 6,290,936 B1 * | 9/2001 | Ross | | A61K 8/06 |
| | | | | 424/400 |
| 6,348,694 B1 * | 2/2002 | Gershteyn | | A61B 5/0059 |
| | | | | 250/372 |
| 6,378,906 B1 * | 4/2002 | Pennaz | | C09D 11/50 |
| | | | | 106/31.32 |
| 6,405,867 B1 * | 6/2002 | Moore | | B65D 1/0207 |
| | | | | 206/459.1 |
| 6,588,435 B1 | 7/2003 | Gindi | | |
| 6,733,766 B2 * | 5/2004 | Gott | | A61K 8/29 |
| | | | | 424/401 |
| 6,734,440 B2 * | 5/2004 | Questel | | G01J 1/50 |
| | | | | 250/474.1 |
| 6,929,136 B2 * | 8/2005 | Salazar-Leal | | B65D 51/245 |
| | | | | 116/207 |
| 6,936,824 B2 * | 8/2005 | Takada | | A61B 5/0059 |
| | | | | 250/372 |
| 7,227,153 B2 * | 6/2007 | Yagi | | G01J 1/429 |
| | | | | 250/372 |
| 7,247,140 B2 * | 7/2007 | Ophardt | | G07F 9/02 |
| | | | | 250/372 |
| 7,265,358 B2 * | 9/2007 | Fontaine | | A42B 1/062 |
| | | | | 250/330 |
| 7,270,440 B2 * | 9/2007 | Levy | | A45D 33/32 |
| | | | | 206/385 |
| D571,219 S * | 6/2008 | McCoy | | D9/544 |
| 7,448,767 B2 * | 11/2008 | Zhang | | A45D 34/045 |
| | | | | 362/118 |
| 7,509,839 B2 * | 3/2009 | Duranton | | A45D 33/26 |
| | | | | 206/581 |
| 7,907,477 B2 * | 3/2011 | Puzia | | A61J 7/0472 |
| | | | | 215/230 |
| 7,976,177 B2 | 7/2011 | Dikopf | | |
| 8,210,395 B1 | 7/2012 | Morris | | |
| 8,312,641 B2 * | 11/2012 | Li | | F26B 3/28 |
| | | | | 118/642 |
| 8,729,503 B2 * | 5/2014 | Chiappo | | G01N 21/64 |
| | | | | 250/458.1 |
| 8,857,741 B2 * | 10/2014 | Morikis | | A61K 8/39 |
| | | | | 239/468 |
| 8,897,100 B2 * | 11/2014 | Joo | | G04F 3/06 |
| | | | | 368/109 |
| 9,694,383 B2 | 7/2017 | Jurcevic | | |
| 9,738,428 B2 | 8/2017 | Torres | | |
| 9,744,111 B2 * | 8/2017 | Norman | | A61K 8/37 |
| 9,816,857 B2 | 11/2017 | Rastegar | | |
| 9,963,271 B2 * | 5/2018 | Richter | | B65D 25/34 |
| 2002/0022008 A1 * | 2/2002 | Forest | | A61K 8/19 |
| | | | | 424/59 |
| 2003/0056410 A1 * | 3/2003 | Witkowski | | G09F 3/0288 |
| | | | | 40/310 |
| 2003/0226978 A1 * | 12/2003 | Ribi | | A61K 8/02 |
| | | | | 250/474.1 |
| 2004/0031927 A1 * | 2/2004 | Tsai | | A61B 5/441 |
| | | | | 250/372 |
| 2004/0155199 A1 * | 8/2004 | Su | | G01J 1/429 |
| | | | | 250/372 |
| 2004/0232169 A1 * | 11/2004 | Glover | | B65D 47/0804 |
| | | | | 222/212 |
| 2005/0118123 A1 | 6/2005 | Vaidya | | |
| 2005/0145525 A1 * | 7/2005 | Williams | | B65D 43/02 |
| | | | | 206/459.1 |
| 2005/0285050 A1 * | 12/2005 | Bruce | | G01J 1/429 |
| | | | | 250/474.1 |
| 2006/0067896 A1 * | 3/2006 | Schaffer | | A61K 8/35 |
| | | | | 424/59 |
| 2006/0133996 A1 | 6/2006 | Haywwood | | |
| 2006/0171770 A1 * | 8/2006 | Bitton | | A45C 15/06 |
| | | | | 401/195 |
| 2006/0244961 A1 * | 11/2006 | Cole | | A61B 5/0071 |
| | | | | 356/319 |
| 2008/0000992 A1 * | 1/2008 | Mediare | | G01K 11/12 |
| | | | | 235/494 |
| 2008/0121816 A1 * | 5/2008 | Ellig | | G01J 1/429 |
| | | | | 250/474.1 |
| 2008/0259315 A1 * | 10/2008 | Mersch | | G01J 1/429 |
| | | | | 356/51 |
| 2008/0260450 A1 * | 10/2008 | Sanchez | | A45D 33/32 |
| | | | | 401/126 |

(56) References Cited

U.S. PATENT DOCUMENTS

| | | | | |
|---|---|---|---|---|
| 2008/0265170 A1* | 10/2008 | Ales | | A61B 5/0059 250/372 |
| 2008/0296513 A1* | 12/2008 | Ribi | | G01J 1/50 250/474.1 |
| 2009/0284732 A1* | 11/2009 | Vitale | | B65D 23/16 356/51 |
| 2009/0320316 A1* | 12/2009 | Zakai | | A45D 29/00 34/275 |
| 2010/0044253 A1 | 2/2010 | Santalucia | | |
| 2010/0163749 A1* | 7/2010 | Hunwick, III | | G01K 11/12 250/474.1 |
| 2010/0213212 A1 | 8/2010 | Custodis | | |
| 2010/0226861 A1 | 9/2010 | Cole | | |
| 2011/0091263 A1* | 4/2011 | von Eberstein | | A45D 33/32 401/129 |
| 2012/0153179 A1* | 6/2012 | Tew | | B05B 11/3042 250/372 |
| 2012/0168333 A1* | 7/2012 | Mackay | | A45D 34/00 206/459.1 |
| 2012/0282010 A1* | 11/2012 | Albers | | A45D 34/042 401/129 |
| 2013/0025614 A1* | 1/2013 | Morgan | | A61C 15/043 132/200 |
| 2014/0003037 A1 | 1/2014 | Kuelzow | | |
| 2014/0042341 A1* | 2/2014 | Park | | B05D 3/067 250/492.1 |
| 2014/0219705 A1* | 8/2014 | Posnick | | A45D 33/02 401/270 |
| 2014/0338216 A1* | 11/2014 | Li | | A45D 29/00 34/275 |
| 2014/0341631 A1* | 11/2014 | Cakridas | | A45D 40/24 401/18 |
| 2015/0083934 A1* | 3/2015 | Richter | | G01J 1/50 250/473.1 |
| 2016/0051805 A1* | 2/2016 | Scorzelli | | A61M 35/003 222/153.13 |
| 2016/0157583 A1* | 6/2016 | Winter | | A45D 34/00 215/227 |
| 2016/0220006 A1* | 8/2016 | Le | | A45D 29/18 |

FOREIGN PATENT DOCUMENTS

| | | | | |
|---|---|---|---|---|
| CN | WO 2016126777 A1 * | 8/2016 | | A45D 29/18 |
| EP | 2853811 A1 | 4/2015 | | |
| TW | 2956294 A3 * | 8/2011 | | A45D 40/265 |
| WO | WO2017034360 A1 | 3/2017 | | |

* cited by examiner

CONTAINER WITH LUMINESCENT SUNSCREEN AND CLOSURE WITH ILLUMINATOR

FIELD OF THE INVENTION

This invention relates generally to sunscreens and, in particular, to apparatus and methods for ensuring adequate sunscreen coverage.

BACKGROUND OF THE INVENTION

Sunscreens are an effective way to reduce harmful exposure to the sun's rays, but they are only effective if the skin is adequately covered. Since these products are applied by hand, there is often no way of knowing if body surfaces have been 'missed' during application.

U.S. Pat. No. 5,562,896 discloses a method and device for protecting a body against sunburn involving application of a sunscreen composition capable of fluorescing under black light illumination. The body is viewed under illumination from the black light so as to identify any non-fluorescing, missed external portions of the body to which the sunscreen was not previously applied. However, the "black light" in this case "is well understood in the art to mean ultraviolet lamps of the type which commonly are sold in novelty stores and the like," and the lamps are disposed in a walk-in booth including a mirror for viewing application of the fluorescing sunscreen to a body.

There are also containers with caps that have UV light sources, but such light sources are used for entirely different purposes. One example is US20160220006, entitled "NAIL POLISH BOTTLE CAP WITH INTEGRAL GEL CURING LIGHT." As evident from the title, the purpose of the illumination if for curing nail polish gels, and not for activating a sunscreen to determine coverage.

SUMMARY OF THE INVENTION

This invention is directed to apparatus for ensuring adequate sunscreen protection. The apparatus includes a container including a light-activated sunscreen product, and a closure for the container including a battery, a switch and a light source that causes the light-activated sunscreen product to glow when illuminated with the light source.

The light-activated sunscreen product may include a zinc-oxide-based lotion and a fluorescent substance such as fluorescein dye causing the lotion to glow in any available color when applied to the skin and illuminated by the light source.

The closure may be a cap with a threaded attachment to the container, and the light source may comprise one or more ultraviolet light-emitting diodes. The closure may be a cap with top and side surfaces, and the switch may be positioned on the side of the cap, and the light source on the top of the cap, or vice versa. The switch is preferably a momentary contact switch.

The invention is compatible with spray-on and even roll-on sunscreens, as the illuminator may mounted on or in the cap. In further alternative embodiments, the illuminator may be mounted elsewhere in the container, including the sides or bottom, and may be provided as a stick-on module.

DETAILED DESCRIPTION OF THE PREFERRED EMBODIMENTS

Figure 1:
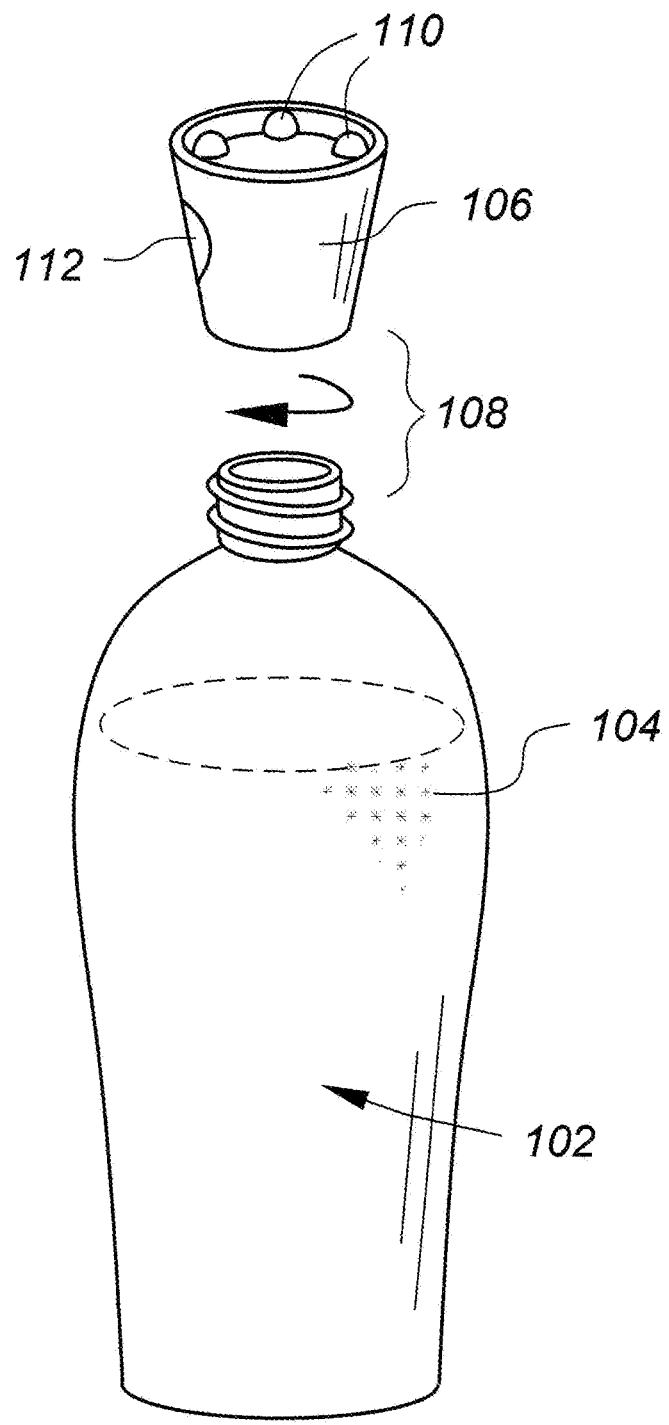
FIG. 1 is a side view of an embodiment of the invention showing a container and cap with UV lights.

FIG. 1 is a side view of an embodiment of the invention depicted generally at 100 including a container 102 and cap 106 with lights 110. The container 102 contains a sunscreen product 104 that includes a light-activated material such as a fluorescent pigment. In accordance with one example, a zinc oxide-based lotion may be used as a physical sunscreen, and the light-activated material may be a fluorescein dye. In a more specific example, I mixed 3 fl. oz. of the sunscreen with 0.5 g of DayGlo DGS-00 pigment, which is a derivative of fluorescein. Those of skill in the art will appreciate that other sunscreens and light-activated materials may be used, and in other quantities, as long as the substance glows when illuminated by lights 110. The combined substance may glow in different colors such as red, green or blue.

Continuing the reference to FIG. 1, the container 102 includes a cap 106 with one or more illumination sources 110. In the preferred embodiment, a plurality of ultraviolet (UV) light-emitting diodes (LEDs) are used as the light sources 110. More preferably, 3-5 NSSU123 UV LEDs form Nichia Corp. are used. See http://www.nichia.co.jp/en/product/uvled.html The cap 106 may screw onto the container 102 by way of a threaded connection 108, though the invention is not limited in terms of the closure mechanism. Nor is the invention limited to the decorative appearance of the container and/or cap shown in the drawings. The container and cap are preferably made of plastic, and the container may be rigid, semi-rigid, or pliable.

Figure 3:
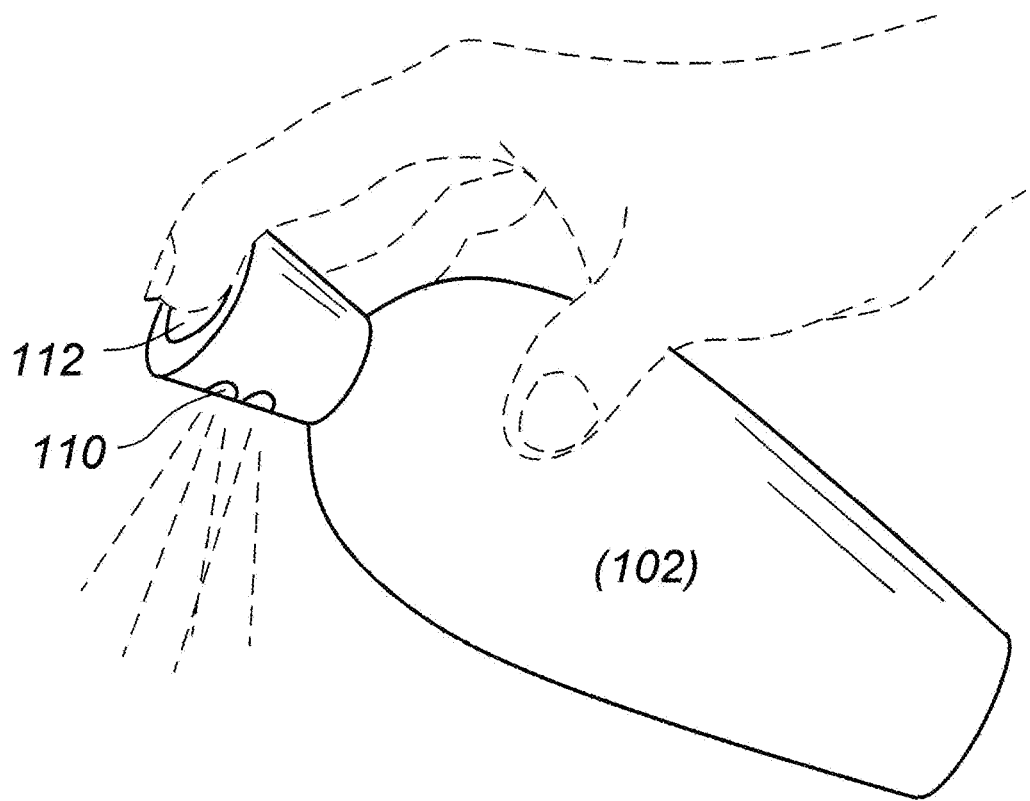
FIG. 3 is a drawing of an alternative embodiment of the invention with a pushbutton on the top of a cap and one or more LEDs on the side of the cap.

The Lights 110 are activated with a switch on the cap. As shown in FIG. 1, the lights 110 are on the top of the cap and the button 112 is on the side. However, either or both components may be positioned elsewhere; for example, the button may be at the top of the cap and the light(s) may be on the side as shown in FIG. 3. The switch is preferably a momentary contact type switch. The cap 106 also houses one or more batteries such as lithium-ion coin cells to power the lights.

Figure 2:
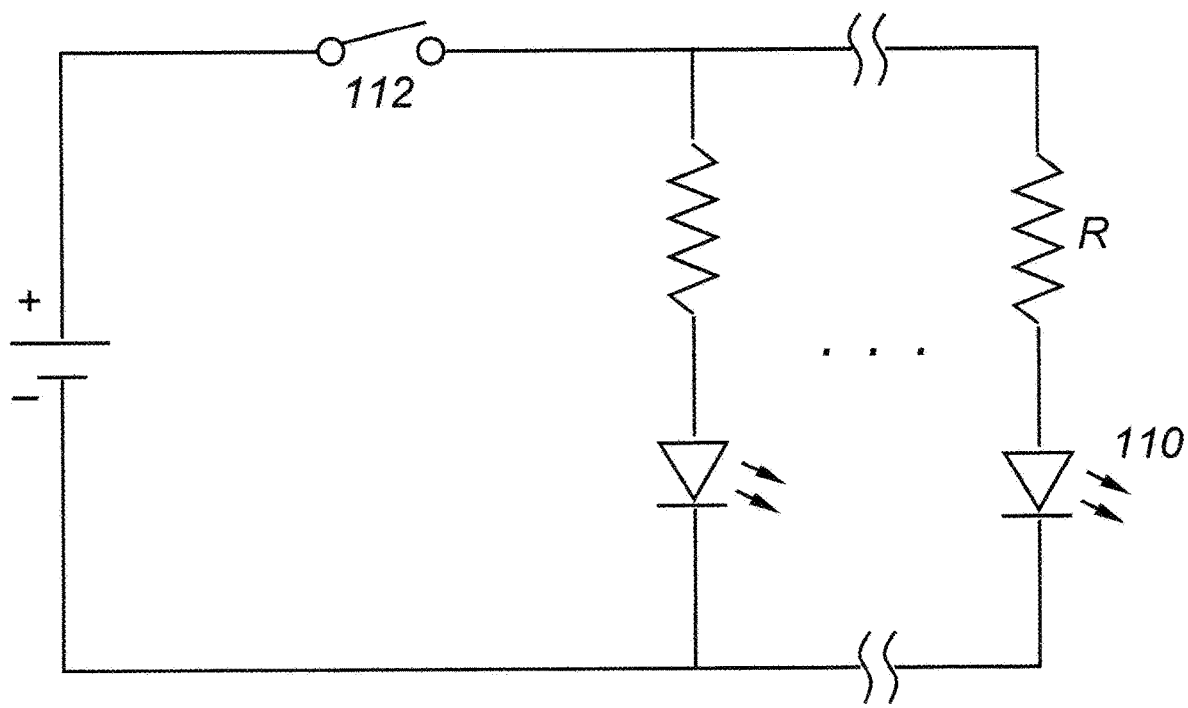
FIG. 2 is a schematic diagram of the circuitry used in the cap.

FIG. 2 is a schematic diagram of the circuitry used to implement the invention. Current-limiting resistors R may be used depending upon the batter(ies) and LED(s) used. While the LEDs are shown in parallel, a series configuration is also possible, depending again upon battery voltage and LED turn-on voltage. The LEDs and resistors may be discrete devices or may be surface-mounted.

Figure 4:
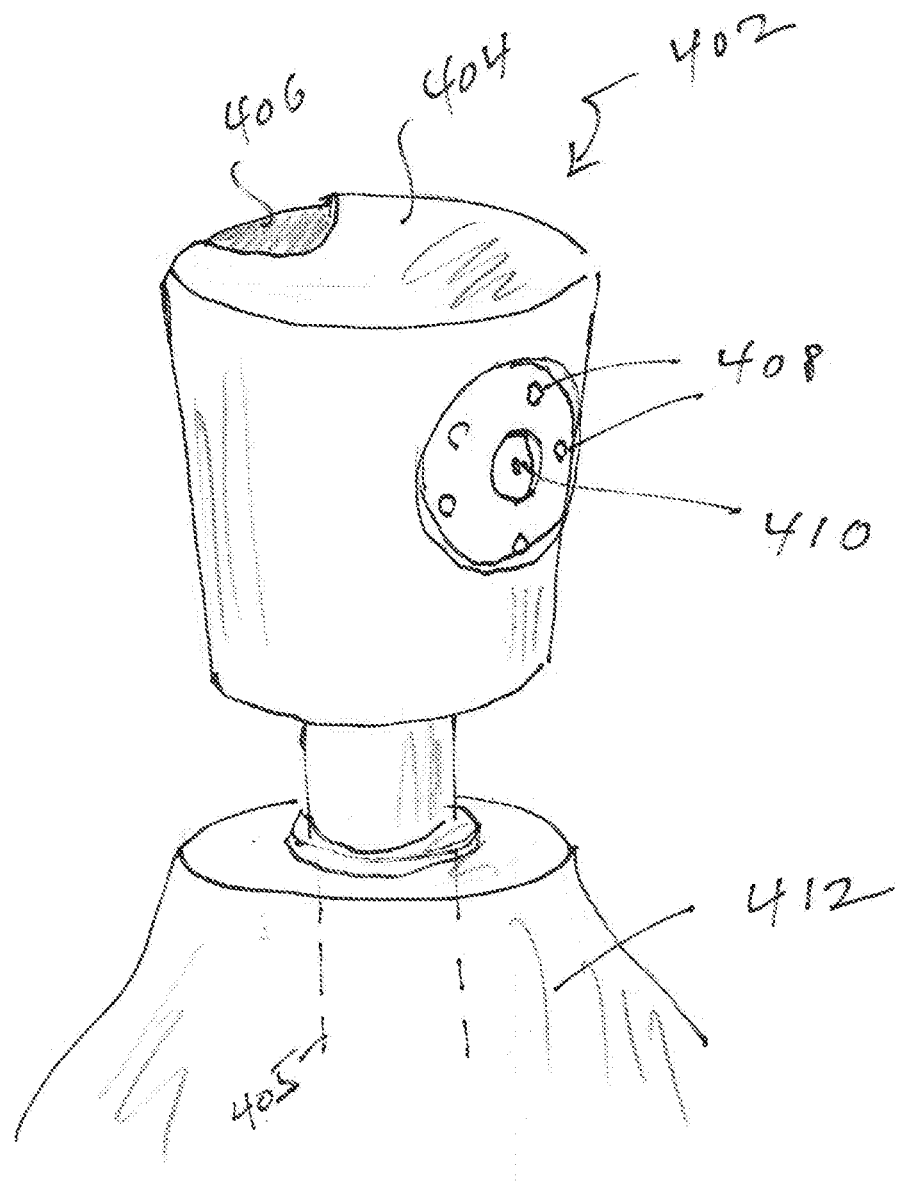
FIG. 4 illustrates an embodiment of the invention utilizing a sunscreen in a spray-on container.

The invention is compatible with different types of closures and caps, including spray-on sunscreens, as shown in FIG. 4. In this embodiment, the cap 402 includes a top surface 404 and pushbutton 406. To spray the sunscreen, a user presses down on the top surface of the cap 402, causing the sunscreen to be drawn up through dip tube 405 and out through orifice 410. T activate the illuminator, a user presses only the switch 406, causing one or more LEDs 408 to be activated. As with other embodiments, circuit 2 is applicable, with components such as the battery being integrated into the cap 402 and not visible in FIG. 4.

In the preferred embodiments, the batteries, circuitry and lotion are selected such that the batteries and illumination last as long as the lotion, at which time the container and cap may be thrown away. In different embodiments, larger batteries may be used, or the batteries may be replaceable and/or rechargeable enabling the same container to be refilled and reused.

The invention claimed is:

1. Apparatus for ensuring adequate sunscreen protection, comprising in combination:
    a container including a light-activated sunscreen product;
    an illuminator physically mounted on the container, the illuminator including a battery, a switch and a light source;
    wherein the light-activated sunscreen product glows with a predetermined color for observation by an unaided eye of a user when illuminated with the light source; and
    wherein the container and illuminator combination does not include a light detector.

2. The apparatus of claim 1, wherein the illuminator is disposed within a closure for the container.

3. The apparatus of claim 2, wherein the closure is a cap to the container.

4. The apparatus of claim 2, wherein the closure is a cap with a threaded attachment to the container.

5. The apparatus of claim 2, wherein:
    the closure is a cap with top and side surfaces; and
    the switch is on the side of the cap and the light source is on the top of the cap, or vice versa.

6. The apparatus of claim 1, wherein the light-activated sunscreen product includes a fluorescent material.

7. The apparatus of claim 1, wherein the light-activated sunscreen product includes fluorescein.

8. The apparatus of claim 1, wherein the light-activated sunscreen product is a zinc-oxide-based lotion including a light-activated material.

9. The apparatus of claim 1, wherein the light source comprises one or more ultraviolet light-emitting diodes.

10. The apparatus of claim 1, wherein the switch is a momentary contact switch.

11. The apparatus of claim 1, wherein the predetermined color is red, green or blue.

12. A method of ensuring adequate sunscreen coverage, comprising the steps of:
    providing a container with a light-activated sunscreen lotion, and wherein the container includes an integrated illuminator further comprising a battery, a switch and a light source;
    wherein the container and the integrated illuminator combination does not include a light detector;
    spreading a portion of the sunscreen lotion onto an area of a person's skin;
    shining the light source onto the area, thereby causing the light-activated substance to glow with a predetermined color; and
    observing the glow with an unaided eye of a user to determine the coverage of the lotion on the skin.

13. The method of claim 12, wherein:
    the illuminator includes a switch for activating a light source; and
    using the switch to shine the light onto the area.

14. The method of claim 13, wherein the light source is an ultraviolet light-emitting diode.

15. The method of claim 12, wherein the sunscreen lotion is zinc-oxide-based.

16. The method of claim 12, wherein the light-activated substance is a fluorescent substance.

17. The method of claim 12, wherein the light-activated substance is fluorescein.

18. The method of claim 12, wherein the illuminator is disposed on a closure or cap for the container.

19. The method of claim 12, wherein the predetermined color is red, green or blue.

\* \* \* \* \*